US011241496B2

(12) United States Patent
Weiner et al.

(10) Patent No.: US 11,241,496 B2
(45) Date of Patent: *Feb. 8, 2022

(54) COMPOSITIONS, COMPRISING IMPROVED IL-12 GENETIC CONSTRUCTS AND VACCINES, IMMUNOTHERAPEUTICS AND METHODS OF USING THE SAME

(71) Applicant: The Trustees of the University of Pennsylvania, Philadelphia, PA (US)

(72) Inventors: David Weiner, Merion, PA (US); Matthew P. Morrow, Bala Cynwyd, PA (US); Jian Yan, Wallingford, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/974,982

(22) Filed: May 9, 2018

(65) Prior Publication Data

US 2018/0333485 A1    Nov. 22, 2018

Related U.S. Application Data

(63) Continuation of application No. 15/055,002, filed on Feb. 26, 2016, now Pat. No. 9,981,036, which is a continuation of application No. 14/365,086, filed as application No. PCT/US2012/069017 on Dec. 11, 2012, now Pat. No. 9,272,024.

(60) Provisional application No. 61/569,600, filed on Dec. 12, 2011.

(51) Int. Cl.

| *C12N 15/63* | (2006.01) |
|---|---|
| *C12P 21/02* | (2006.01) |
| *C07K 14/54* | (2006.01) |
| *A61K 38/20* | (2006.01) |
| *A61K 39/39* | (2006.01) |
| *A61K 39/00* | (2006.01) |
| *A61K 39/245* | (2006.01) |
| *C12N 7/00* | (2006.01) |
| *A61K 39/29* | (2006.01) |
| *A61K 41/00* | (2020.01) |
| *A61K 39/395* | (2006.01) |
| *C12N 5/10* | (2006.01) |
| *C12N 7/02* | (2006.01) |

(52) U.S. Cl.
CPC .............. *A61K 39/39* (2013.01); *A61K 38/20* (2013.01); *A61K 38/208* (2013.01); *A61K 38/2086* (2013.01); *A61K 39/0005* (2013.01); *A61K 39/00114* (2018.08); *A61K 39/245* (2013.01); *A61K 39/292* (2013.01); *A61K 41/00* (2013.01); *C07K 14/5434* (2013.01); *C12N 7/00* (2013.01); *A61K 2039/525* (2013.01); *A61K 2039/53* (2013.01); *A61K 2039/55538* (2013.01); *C12N 2510/00* (2013.01); *C12N 2710/16034* (2013.01); *C12N 2730/10134* (2013.01); *C12N 2730/10171* (2013.01)

(58) Field of Classification Search
None
See application file for complete search history.

(56) References Cited

U.S. PATENT DOCUMENTS

| 6,096,869 A | 8/2000 | Stanley |
|---|---|---|
| 7,833,754 B2 | 11/2010 | Felber |
| 8,026,223 B1 | 9/2011 | Heller |
| 9,272,024 B2 | 3/2016 | Weiner |
| 2003/0181405 A1 | 9/2003 | Nordstrom |

FOREIGN PATENT DOCUMENTS

| CN | 1798502 A | 7/2006 |
|---|---|---|
| EP | 2791157 A1 | 10/2014 |
| WO | 9947678 A2 | 9/1999 |
| WO | 2007084364 A2 | 7/2007 |
| WO | 2008089144 A2 | 7/2008 |
| WO | 2010126766 A1 | 11/2010 |
| WO | 2013090296 | 6/2013 |

OTHER PUBLICATIONS

Wells, 1990, Biochemistry 29:8509-8517.*
Bork, 2000, Genome Research 10:398-400.*
Skolnick et al., 2000, Trends in Biotech. 18(1):34-39.*
Doerks et al., 1998, Trends in Genetics 14:248-250.*
Tokuriki and Tawflik, Current Opinion in Structural Biology 2009, 19: 596-604.*
Canadian Examiner Requisition for Application No. CA2,858,893, dated Nov. 19, 2019, 4 pages.
Jalah et al. 'The p40 Subunit of Interleukin (IL)-12 Promotes Stabilization and Export of the p35 Subunit: Implications for Improved IL-12 Cytokine Production', Journal of Biological Chemistry, Mar. 1, 2013, vol. 288, No. 9 pp. 6763-6776.
Korean Office Action for KR10-2014-7019094 dated Jan. 8, 2019, 5 pages.

(Continued)

*Primary Examiner* — Bridget E Bunner
*Assistant Examiner* — Fozia M Hamud
(74) *Attorney, Agent, or Firm* — Riverside Law LLP

(57) ABSTRACT

Nucleic acid molecules and compositions comprising: a nucleic acid sequence that encodes IL-12 p35 subunit or a functional fragment thereof and/or a nucleic acid sequence that encodes IL12 p40 subunit or a functional fragment thereof, are disclosed. The nucleic acid molecules and compositions further comprising a nucleic acid sequence that encodes an immunogen are also disclosed. Method of modulating immune response and methods of inducing an immune response against an immunogen are disclosed. Therapeutic and prophylactic vaccination methods are also disclosed.

18 Claims, 3 Drawing Sheets

Specification includes a Sequence Listing.

(56) References Cited

OTHER PUBLICATIONS

Leong et al., "Optimized expression and specific activity of IL-12 by directed molecular evolution", PNAS, Feb. 4, 2003; vol. 100, No. 3, pp. 1163-1168, www.pnas.org/cgi/doi/10.1073/pnas.

McMonagle et al., "Production of biologically active equine interleukin 12 through expression of p35, p40 and single chain IL-12 in mammalian and baculovirus expression systems" 2001, Equine Vet. J., 33:693-698.

Notice of Allowance dated Jan. 25, 2018 for U.S. Appl. No. 15/055,002; (pp. 1-7).

Office Action dated Dec. 23, 2019 for U.S. Appl. No. 15/974,982 (pp. 1-24).

Office Action dated Jun. 25, 2019 for U.S. Appl. No. 15/974,982 (pp. 1-20).

Patel V et al: 'Long-lasting humoral and cellular immune responses and mucosal dissemination after intramuscular DNA immunization,' Vaccine, 28(30): 4827-4836, Jul. 5, 2010.

S.G. Hansen et al: "Cytomegalovirus Vectors Violate CD8+ T Cell Epitope Recognition Paradigms," Science, May 24, 2013, 340(6135):1237874-1-1237874-17.

\* cited by examiner

Figure 3

Anti-HBV T Cell Responses (By ELISpot)
1 mg each antigen, .04mg pMacIL-12-opt Increased magnitude and expansion of responses to Core and surface antigens with pMacIL-12-opt

SEQUENCE LISTING

<160> NUMBER OF SEQ ID NOS: 5

<210> SEQ ID NO 1
<211> LENGTH: 660
<212> TYPE: DNA
<213> ORGANISM: Artificial Sequence
<220> FEATURE:
<223> OTHER INFORMATION: IL-12 Optimized p35 subunit nucleic acid

<400> SEQUENCE: 1

```
atgtgccccg ctcggtccct gctgctggtc gctaccctgg tcctgctgga tcacctgtca    60
ctggctcgaa atctgcctgt cgctaccccc gatcctggca tgttccoctg cctgcaccat   120
agccagaacc tgctgcgggc cgtgtccaat atgctgcaga aagctagaca gacactggag   180
ttttacccctt gtacttctga ggaaatcgac acgaggata ttactaagga caaaacctcc   240
acagtcgaag cctgcctgcc actggagctg accaagaacg aatcatgtct gaatagcagg   300
gagacttcct tcatcaccaa cgggtcttgc ctggctagtc gcaagaccag cttcatgatg   360
gcactgtgcc tgagctccat ctacgaggat ctgaagatgt atcaggtgga attcaaaacc   420
atgaacgcta agctgctgat ggaccctaaa cgacagatct tctgggatca gaatatgctg   480
gcagtgattg acgagctgat gcaggccctg aacttcaata gcgaaaccgt cccacagaag   540
tctagtctgg aggaacccga ctttttataag acaaaaatca agctgtgcat tctgctgcat   600
gcctttcgga ttcgggctgt cactattgat cgggtcatgt catacctgaa cgcttcctaa   660
```

<210> SEQ ID NO 2
<211> LENGTH: 219
<212> TYPE: PRT
<213> ORGANISM: Artificial Sequence
<220> FEATURE:
<223> OTHER INFORMATION: IL-12 Opt p35 subunit amino acid

<400> SEQUENCE: 2

```
Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala
            100                 105                 110

Ser Arg Lys Thr Ser Phe Met Met Ala Leu Cys Leu Ser Ser Ile Tyr
        115                 120                 125

Glu Asp Leu Lys Met Tyr Gln Val Glu Phe Lys Thr Met Asn Ala Lys
    130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Glu Pro Asp Phe Tyr Lys Thr Lys
            180                 185                 190
```

```
Ile Lys Leu Cys Ile Leu Leu His Ala Phe Arg Ile Arg Ala Val Thr
    195                 200                 205

Ile Asp Arg Val Met Ser Tyr Leu Asn Ala Ser
    210                 215

<210> SEQ ID NO 3
<211> LENGTH: 987
<212> TYPE: DNA
<213> ORGANISM: Artificial Sequence
<220> FEATURE:
<223> OTHER INFORMATION: IL-12 Opt p40 subunit nucleic acid

<400> SEQUENCE: 3
atgtgccatc agcagctggt catctcttgg tttagtctgg tgtttctggc ttctccactg      60
gtcgctatct gggaactgaa aaaggatgtg tacgtggtcg agctggactg gtatccagat     120
gcacccggag aaatggtggt cctgacctgc gacacacccg aggaagatgg catcacttgg     180
accctggacc agagctccga ggtgctggga tctggcaaga cactgactat tcaggtcaaa     240
gaattcgggg atgccggaca gtacacatgt cacaagggcg gggaggtgct gagtcactca     300
ctgctgctgc tgcataagaa agaagacggc atctggtcta ctgacattct gaaggatcag     360
aaagagccta agaacaaaac cttcctgaga tgcgaagcta agaattatag tgggaggttt     420
acctgttggt ggctgaccac aatctcaact gacctgacct ttagcgtgaa atctagtagg     480
gggtcaagcg atccacaggg agtgacctgc ggagcagcta cactgagcgc cgagcgggtg     540
agaggagaca caaggagta cgaatatagt gtcgagtgcc aggaagattc agcctgtccc     600
gcagccgagg aatccctgcc tatcgaagtg atggtggacg ctgtgcacaa gctgaaatac     660
gaaaactaca tcctctcttt ctttattcgc gacatcatta gccagatccc cctaaaaaac     720
ctgcagctga gcccctgaa aaattcccga caggtggagg tctcttggga ataccctgat     780
acatggagca ctccacattc ttatttcagt ctgactttt gcgtgcaggt ccagggcaag     840
agcaaaaggg agaagaaaga ccgcgtgttc accgataaga catccgctac tgtcatctgt     900
cgaaaaaacg caagcatttc cgtgcgggca caggataggt attattccag cagttggtct     960
gagtgggctt ccgtcccttg tagttga                                          987

<210> SEQ ID NO 4
<211> LENGTH: 328
<212> TYPE: PRT
<213> ORGANISM: Artificial Sequence
<220> FEATURE:
<223> OTHER INFORMATION: IL-12 Opt p40 subunit amino acid

<400> SEQUENCE: 4

Met Cys His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95
```

```
Leu Ser His Ser Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
            115                 120                 125

Leu Arg Cys Glu Ala Lys Asn Tyr Ser Gly Arg Phe Thr Cys Trp Trp
130                 135                 140

Leu Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
            195                 200                 205

Glu Val Met Val Asp Ala Val His Lys Leu Lys Tyr Glu Asn Tyr Thr
            210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
            275                 280                 285

Val Phe Thr Asp Lys Thr Ser Ala Thr Val Ile Cys Arg Lys Asn Ala
            290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 5
<211> LENGTH: 18
<212> TYPE: PRT
<213> ORGANISM: Artificial Sequence
<220> FEATURE:
<223> OTHER INFORMATION: IgE leader

<400> SEQUENCE: 5

Met Asp Trp Thr Trp Ile Leu Phe Leu Val Ala Ala Thr Arg Val
1               5                   10                  15

His Ser
```

COMPOSITIONS, COMPRISING IMPROVED IL-12 GENETIC CONSTRUCTS AND VACCINES, IMMUNOTHERAPEUTICS AND METHODS OF USING THE SAME

CROSS-REFERENCE TO RELATED APPLICATIONS

This is a continuation application claiming benefit to U.S. application Ser. No. 15/055,002, filed Feb. 26, 2016, issued as U.S. Pat. No. 9,981,036, which is a continuation application claiming benefit to U.S. application Ser. No. 14/365,086, filed Jun. 12, 2014, issued as U.S. Pat. No. 9,272,024, which is the U.S. national stage application filed under 35 U.S.C. § 371 claiming benefit to International Patent Application No. PCT/US12/069,017, filed Dec. 11, 2012, which is entitled to priority under 35 U.S.C. § 119(e) to U.S. Provisional Application No. 61/569,600, filed Dec. 12, 2012, each of which is hereby incorporated by reference in its entirety.

FIELD OF THE INVENTION

The present invention relates to improved genetic constructs that encode human IL-12 and nucleic acid molecules which comprise the same. The present invention also relates to improved expression vectors, vaccines and immunotherapeutics which include nucleotide sequences that encode human Il-12 and to methods of using the same.

BACKGROUND OF THE INVENTION

Immunotherapy refers to modulating a person's immune responses to impart a desirable therapeutic effect. Immunotherapeutics refer to those compositions which, when administered to an individual, modulate the individual's immune system sufficient to ultimately decrease symptoms which are associated with undesirable immune responses or to ultimately alleviate symptoms by increasing desirable immune responses. In some cases, immunotherapy is part of a vaccination protocol in which the individual is administered a vaccine that exposes the individual to an immunogen against which the individual generates an immune response in such cases, the immunotherapeutic increases the immune response and/or selectively enhances a portion of the immune response (such as the cellular arm or the humoral arm) which is desirable to treat or prevent the particular condition, infection or disease.

In designing vaccines, it has been recognized that vaccines that produce the target antigen in cells of the vaccinated individual are effective in inducing the cellular arm of the immune system. Specifically, live attenuated vaccines, recombinant vaccines which use avirulent vectors and DNA vaccines each lead to the production of antigens in the cell of the vaccinated individual which results in induction of the cellular arm of the immune system. On the other hand, killed or inactivated vaccines, and sub-unit vaccines which comprise only proteins do not induce good cellular immune responses although they do induce an effective humoral response.

A cellular immune response is often necessary to provide protection against pathogen infection and to provide effective immune-mediated therapy for treatment of pathogen infection, cancer or autoimmune diseases. Accordingly, vaccines that produce the target antigen in cells of the vaccinated individual such as live attenuated vaccines, recombinant vaccines that use avirulent vectors and DNA vaccines are often preferred.

There is a need for vaccine approaches that can induce strong T cell and B cell immunity in humans. Recent concerns over attenuation, vaccine manufacturing complexity, serological interference, as was observed in the HIV STEP trial, among a host of other issues serve to underscore this important issue. In non-human primate models and in human clinical trials, simple plasmid DNA as a vaccine platform has not induced levels of immunogenicity satisfactory for commercial development efforts to be supported. In head to head comparisons some naked plasmid-based vaccines did not induce either cellular or humoral responses comparable to those induced by their viral vector counterparts, including the commonly used adenovirus serotype 5 (Ad5) platform.

The development of DNA vaccine technology as a stand-alone method of vaccination, as well as its utility in current prime-boost platforms, would benefit by the development of strategies to enhance its immune potency. The manipulation of codon and RNA encoding sequences as well as changes in leader sequences have been reported to enhance the expression of plasmid-encoded immunogens. In addition, the creation of consensus immunogens attempts to address the need for broad immunological coverage to account in part for viral diversity.

In addition, other strategies have been employed that focus on improving the physical delivery of DNA plasmids by improving formulations and device driven technologies. DNA vaccines delivered by electroporation (EP) have been reported to enhance antigen-specific interferon-γ (IFNγ) production following immunization of plasmid DNA in rhesus macaques.

The co-delivery of plasmid-encoded molecular adjuvants to augment vaccine-induced responses is another important area of this specific investigation. One of the best-characterized molecular adjuvants in non-human primates is IL-12, a $T_H1$ polarizing cytokine that drives CTL responses by providing the "third signal" needed for efficient activation and antigen-specific expansion of naive CD8$^+$ T cells. IL-12 is a heterodimer which contains two subunits, p35 and p40. It has been shown to be the most impressive immune enhancing cytokine, particularly for driving CD8 T cells when engineered as a DNA vaccine. In macaques, IL-12 has been shown to be an adjuvant that is highly potent for expanding the cellular Immune potency of a DNA vaccine targeting multiple antigens. In both macaques as well and in humans such a DNA vaccine adjuvant can significantly improve the immune responses induced by a DNA vaccine.

U.S. Pat. No. 5,723,127, which is incorporated herein by reference, discloses IL-12 as a vaccine adjuvant. PCT application no. PCT/US1997/019502 and corresponding U.S. Application Ser. No. 08/956,865, which is incorporated herein by reference, discloses DNA vaccines and DNA constructs comprising IL-12 coding sequences.

There remains a need for improved vaccines and immunotherapeutics. There is a need for compositions and methods that produce enhanced immune responses. Likewise, while some immunotherapeutics are useful to modulate immune response in a patient there remains a need for improved immunotherapeutic compositions and methods. There remains a need for improved constructs which encode IL-12 and can be used as part of DNA vaccine strategies. There remains a need for improved constructs which encode IL-12 and can be used as an immunotherapeutic. There remains a need for improved constructs which encode IL-12 and can be used to achieve high levels of expression of IL-12.

SUMMARY OF THE INVENTION

Compositions are provided that comprises a nucleic acid sequence that encodes IL-12 p35 subunit or a functional fragment thereof and a nucleic acid sequence that encodes IL-12 p40 subunit or a functional fragment thereof. Nucleic acid sequences that encodes IL-12 p35 subunit may be at least 98% homologous to SEQ ID NO:1 and encode a protein at least 98% homologous to SEQ ID NO:2. Nucleic acid sequences that encodes functional fragment of IL-12 p35 subunit may be fragments of a nucleic acid sequence that is at least 98% homologous to SEQ ID NO:1 and encodes a protein at least 98% homologous to a functional fragment of SEQ ID NO:2. Nucleic acid sequences that encodes IL-12 p40 subunit may be at least 98% homologous to SEQ ID NO:3 and encode a protein at least 98% homologous to SEQ ID NO:4. Nucleic acid sequences that encodes functional fragment of IL-12 p40 subunit may be fragments of a nucleic acid sequence that is at least 98% homologous to SEQ ID NO:3 and encodes a protein at least 98% homologous to a functional fragment of SEQ ID NO:4. Compositions may further comprise a nucleic acid sequence that encodes an immunogen.

Method of modulating immune response are also provided. The methods comprise the step of administering to an individual, a composition that comprises a nucleic acid sequence that encodes IL-12 p35 subunit or a functional fragment thereof and a nucleic acid sequence that encodes IL-12 p40 subunit or a functional fragment thereof.

Method of inducing an immune response against an immunogen are also provided. The methods comprise the step of administering to an individual, a composition that encodes IL-12 p35 subunit or a functional fragment thereof and a nucleic acid sequence that encodes IL-12 p40 subunit or a functional fragment thereof in combination with a nucleic acid sequence that encodes an immunogen in an amount. The methods of inducing an immune response against an immunogen may be part of methods of inducing a therapeutic immune response or methods of inducing a prophylactic immune response.

BRIEF DESCRIPTION OF THE DRAWINGS

FIG. 3 shows the enhanced HBV core and surface antigen-specific cellular immune responses in rhesus macaques.

DETAILED DESCRIPTION OF THE PREFERRED EMBODIMENT

Figure 1A:
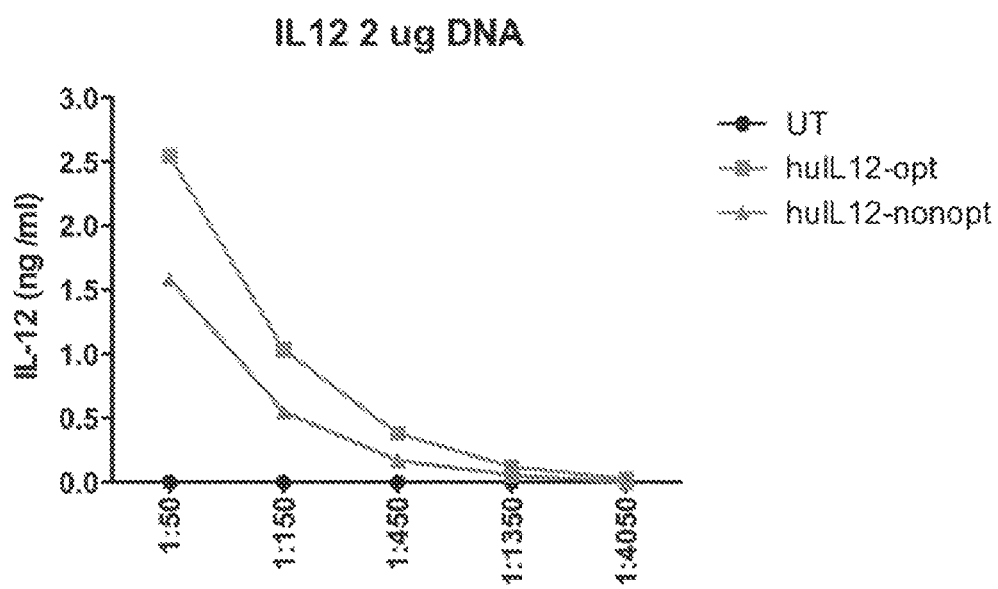
FIGS. 1A and 1B shows a graph comparing expression levels of human IL-12 in cells transfected with 2 μg HuIL12-opt or HuIL12-nonopt (FIG. 1A) or 4 μg HuIL12-opt and HuIL12-nonopt (FIG. 1B).

In one aspect of the invention, it is desired that the improved IL-12 constructs provides for improved transcription and translation, including having one or more of the following: low GC content leader sequence to increase transcription; mRNA stability and codon optimization; eliminating to the extent possible cis-acting sequence motifs (i.e., internal TATA-boxes).

In some aspects of the invention, it is desired to incorporate the improved IL-12 constructs into a vaccine regimen, either as part of the vaccine composition or as a separate composition delivered in a coordinated fashion with the vaccine in order to generate a broad immune against vaccine immunogens. In some aspects of the invention, it is desired to provide the improved IL-12 constructs as an immunotherapeutic which can be used to modulate immune responses in an individual. In some aspects of the invention, it is desired to provide the improved IL-12 constructs in order to provide expression vectors which can be used to obtain high levels of IL-12 expression.

Higher potency IL-12 gene adjuvants are provided herein. These new adjuvants have several advantages over older IL-12 molecules. An enhanced leader sequence that facilitates secretion of the molecules as well as improves ribosome loading is provided, thus expanding the impact of these adjuvants and increasing expression. Significant changes to the RNA sequences further removes homology to native IL-12 sequences thus preventing interference between the delivered adjuvant and the host system, as well as lowering possible deleterious interactions between the host IL-12 sequences and the gene delivered molecules. Furthermore the higher potency of the new constructs lowers the dose requirement thus improving manufacturing as well as delivery issues associated with such adjuvants. Finally as these molecules have more bioactivity, they improve performance of the vaccine in vivo. Together these are important new tools for vaccine as well as immune therapy applications.

1. Definitions.

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6,9, and 7.0 are explicitly contemplated.

a. Adjuvant

"Adjuvant" as used herein may mean a molecule, including a nucleic acid molecule that encodes a protein having immunomodulating activity, added to DNA plasmid vaccines or other vaccines to enhance antigenicity of the one or more antigens encoded by the DNA plasmids or vaccines, and nucleic acid sequences that encode the adjuvant protein described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered.

d. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

e. Constant Current

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

f. Current Feedback or Feedback

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

g. Decentralized Current

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

h. Electroporation

"Electroporation," "electro-permeabilization," or "electro-kinetic enhancement" ("EP") as used interchangeably herein may refer to the use of a transmembrane electric field pulse to induce microscopic pathways (pores) in a biomembrane; their presence allows biomolecules such as plasmids, oligonucleotides, siRNA, drugs, ions, and water to pass from one side of the cellular membrane to the other.

i. Feedback Mechanism

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

j. Fragment

"Fragment" as used herein may mean a portion or a nucleic acid that encodes a polypeptide capable of eliciting an immune response in a mammal substantially similar to that of the non-fragment for The fragments may be DNA fragments selected from fragments of SEQ ID NO:1, fragments of a nucleic acid sequence that is at least 98% homologous to SEQ ID NO:1 and encodes a function fragments of a protein that is at least 98% homologous to SEQ ID NO:2; fragments of SEQ ID NO:3, and fragments of a nucleic acid sequence that is at least 98% homologous to SEQ ID NO:3 and encodes a function fragments of a protein that is at least 98% homologous to SEQ ID NO:4.

The DNA fragments of SEQ ID NO:1, fragments of a nucleic acid sequence that is at least 98% homologous to SEQ ID NO:1 and encodes a function fragments of a protein that is at least 98% homologous to SEQ ID NO:2 may encodes 50 or more amino acids in length, 55 or more, 60 or more, 65 or more, 70 or more, 75 or more, 80 or more, 85 or more, 90 or more, 95 or more, 100 or more, 105 or more, 110 or more, 115 or more, 120 or more, 125 or more, 130 or more, 135 or more, 140 or more, 145 or more, 150 or more, 155 or more, 160 or more, 165 or more, 170 or more, 175 or more, 180 or more, 185 or more, 190 or more, 195 or more, 200 or more, 205 or more, 210 or more in length or 215 or more of SEQ ID NO:2 or a protein that is at least 98% homologous to SEQ ID NO:2 The DNA fragments of SEQ TD NO:1, fragments of a nucleic acid sequence that is at least 98% homologous to SEQ ID NO:1 and encodes a function fragments of a protein that is fewer than 53, fewer than 58, fewer than 63, fewer than 68, fewer than 73, fewer than 78, fewer than 83, fewer than 88, fewer than 93, fewer than 98, fewer than 103, fewer than 108, fewer than 113, fewer than 118, fewer than 123, fewer than 128, fewer than 133, fewer than 138, fewer than 143, fewer than 148, fewer than 153, fewer than 158, fewer than 163, fewer than 168, fewer than 173, fewer than 178, fewer than 183, fewer than 188, fewer than 193, fewer than 198, fewer than 203, fewer than 208, fewer than 213 or fewer than 218 amino acids in length of SEQ ID NO:2 or a protein that is at least 98% homologous to SEQ ID NO:2. In some embodiments, the fragments of a nucleic acid sequence that is at least 98% homologous to SEQ ID NO:1 encodes functional fragments of a protein that is at least 98% homologous to SEQ ID NO:2. In some embodiments, the fragments of a nucleic acid sequence that is at least 98% homologous to SEQ ID NO:1 encodes functional fragments of a protein that is at least 99% homologous to SEQ ID NO:2. In some embodiments, the fragments of a nucleic acid sequence that is at least 98% homologous to SEQ ID NO:1 encodes functional fragments of SEQ ID NO:2. In some embodiments, the fragments of a nucleic acid sequence that is at least 99% homologous to SEQ ID NO:1 encodes functional fragments of a protein that is at least 98% homologous to SEQ ID NO:2. In some embodiments, the fragments of a nucleic acid sequence that is at least 99% homologous to SEQ ID NO:1 encodes functional fragments of a protein that is at least 99% homologous to SEQ ID NO:2. In some embodiments, the fragments of a nucleic acid sequence that is at least 99% homologous to SEQ ID NO:1 encodes functional fragments of SEQ ID NO:2. In some embodiments, the fragments are fragments of SEQ ID NO:1 that encode functional fragments of SEQ ID NO:2.

The DNA fragments of SEQ ID NO:3, fragments of a nucleic acid sequence that is at least 98% homologous to SEQ ID NO:3 and encodes a function fragments of a protein that is at least 98% homologous to SEQ ID NO:4 may encodes 50 or more amino acids in length, 55 or more, 60 or more, 65 or more, 70 or more, 75 or more, 80 or more, 85 or more, 90 or more, 95 or more, 100 or more, 105 or more, 110 or more, 115 or more, 120 or more, 125 or more, 130 or more, 135 or more, 140 or more, 145 or more, 150 or more, 155 or more, 160 or more, 165 or more, 170 or more, 175 or more, 180 or more, 185 or more, 190 or more, 195 or more, 200 or more, 205 or more, 210 or more, 215 or more, 220 or more, 225 or more, 230 or more, 235 or more, 240 or more, 245 or more, 250 or more, 255 or more, 260 or more, 265 or more, 270 or more, 275 or more, 280 or more, 285 or more, 290 or more, 295 or more, 300 or more, 305 or more, 310 or more, 315 or more, 320 or more, or 325 or more amino acids of SEQ ID NO:4 or of a protein that is at least 98% homologous to SEQ ID NO:4 The DNA fragments of SEQ ID NO:3 and fragments of a nucleic acid sequence that is at least 98% homologous to SEQ ID NO:3 may encode a function fragments that is fewer than 53, fewer than 58, fewer than 63, fewer than 68, fewer than 73, fewer than 78, fewer than 83, fewer than 88, fewer than 93, fewer than 98, fewer than 103, fewer than 108, fewer than 113, fewer than 118, fewer than 123, fewer than 128, fewer than 133, fewer than 138, fewer than 143, fewer than 148, fewer than 153, fewer than 158, fewer than 163, fewer than 168, fewer than 173, fewer than 178, fewer than 183, fewer than 188, fewer than 193, fewer than 198, fewer than 203, fewer than 208, fewer than 213, fewer than 218, fewer than 223, fewer than 228, fewer than 233, fewer than 238, fewer than 243, fewer than 248, fewer than 253, fewer than 258, fewer than 263, fewer than 268, fewer than 273, fewer than 278, fewer than 283, fewer than 288, fewer than 293, fewer than 298, fewer than 303, fewer than 308, fewer than 313, fewer than 318 or fewer than 328 amino acids SEQ ID NO:4 or a protein that is at least 98% homologous to SEQ ID NO:4. In some embodiments, the fragments of a nucleic acid sequence that is at least 98% homologous to SEQ ID NO:3 encodes functional fragments of a protein that is at least 98% homologous to SEQ ID NO:4. In some embodiments, the fragments of a nucleic acid sequence that is at least 98% homologous to SEQ ID NO:3 encodes functional fragments of a protein that is at least 99% homologous to SEQ ID NO:4. In some embodiments, the fragments of a nucleic acid sequence that is at least 98% homologous to SEQ ID NO:3 encodes functional fragments of SEQ ID NO:4. In some embodiments, the fragments of a nucleic acid sequence that is at least 99% homologous to SEQ ID NO:3 encodes functional fragments of a protein that is at least 98% homologous to SEQ ID NO:4. In some embodiments, the fragments of a nucleic acid sequence that is at least 99% homologous to SEQ ID NO:3 encodes functional fragments of a protein that is at least 99% homologous to SEQ ID NO:4. In some embodiments, the fragments of a nucleic acid sequence that is at least 99% homologous to SEQ ID NO:3 encodes functional fragments of SEQ ID NO:4. In some embodiments, the fragments are fragments of SEQ ID NO:3 that encode functional fragments of SEQ ID NO:4.

DNA fragments may be free of coding sequences for IL-12 signal peptide. DNA fragments may comprise coding sequences for the immunoglobulin signal peptide such as IgE or IgG signal peptide sequences. Thus for example, DNA fragments that encode an IL-12 p35 subunit not encode amino acids 1-22 of SEQ ID NO:2 and, in some such embodiments, may comprises sequences that encode an immunoglobulin signal peptide such as IgE signal peptide sequence (SEQ ID NO:5) or IgG signal peptide sequence.

"Fragment" may also refer to polypeptide fragments capable of functioning substantially similar to that of the full length polypeptide. The fragment of IL-12 p35 may be a fragment of SEQ ID NO:2 or a fragment of a polypeptide that is at least 98% homologous to a fragment of SEQ ID NO:2. The fragment of IL-12 p35 may be a fragment of a polypeptide that is at least 99% homologous to a fragment of SEQ ID NO:2. The fragment of IL-12 p35 may be a fragment as described above. The fragment of IL-12 p40 may be a fragment of SEQ ID NO:4 or a fragment of a polypeptide that is at least 98% homologous to a fragment of SEQ ID NO:4. The fragment of IL-12 p40 may be a fragment of a polypeptide that is at least 99% homologous to a fragment of SEQ ID NO:4. The fragment of IL-12 p40 may be a fragment as described above.

A "functional fragment" is meant to refer to a fragment of an IL-12 subunit that less than complete p35 and/or less than complete p40 sequence, that, can function substantially similarly to full length p35 or p40. Such substantially similar function includes interaction with other proteins, subunits and receptors in a substantially same manner as the full length p35 or p40 and when delivered in a manner that allows for formation of a heterodimer results in substantially the same effect as the IL-12 p35/p40 heterodimer.

k. Genetic Construct

The term "genetic construct" as used herein refers to the DNA or RNA molecules that comprise a nucleotide sequence which encodes one or both IL-12 subunits or a target protein or another (non-IL-12) immunomodulating protein. The coding sequence includes initiation and termination signals operably linked to regulatory elements including a promoter and polyadenylation signal capable of directing expression in the cells of the individual to whom the nucleic acid molecule is administered.

l. Hyperproliferative

As used herein, the term "hyperproliferative diseases" is meant to refer to those diseases and disorders characterized by hyperproliferation of cells and the term "hyperproliferative-associated protein" is meant to refer to proteins that are associated with a hyperproliferative disease.

m. Identical

"Identical" or "identity" as used herein in the context of two or more nucleic acids or polypeptide sequences, may mean that the sequences have a specified percentage of residues that arc the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

n. Impedance

"Impedance" as used herein may be used when discussing the feedback mechanism and can be converted to a current value according to Ohm's law, thus enabling comparisons with the preset current.

o. Immune Response

"Immune response" as used herein may mean the activation of a host's immune system, e.g., that of a mammal, in response to the introduction of one or more RSV consensus antigen via the provided DNA plasmid vaccines. The immune response can be in the form of a cellular or humoral response, or both.

p. Intracellular Pathogen

"Intracellular pathogen" as used herein, is meant to refer to a virus or pathogenic organism that, at least part of its reproductive or life cycle, exists within a host cell and therein produces or causes to be produced, pathogen proteins.

q. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribo-nucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

r. Operably Linked

"Operably linked" as used herein when referring to a gene operably linked to a promoter refers to the linkage of the two components such that expression of the gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function. When referring to a signal peptide operable linked to a protein, the term refers to the protein having the signal peptide incorporated as part of the protein in a manner that it can function as a signal peptide. When referring to coding sequence that encodes a signal peptide operable linked to coding sequence that encodes a protein, the term refers to the coding sequences arranged such that the translation of the coding sequence produces a protein having the signal peptide incorporated as part of the protein in a manner that it can function as a signal peptide.

s. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

t. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0 M sodium ion, such as about 0.01-1.0 M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5× SSC, and 1% SDS, incubating at 42° C., or, 5× SSC, 1% SDS, incubating at 65° C., with wash in 0.2× SSC, and 0.1% SDS at 65° C.

u. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

v. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

w. Target Protein

"Target protein" as used herein is meant to refer to peptides and protein which are part of vaccines or which are encoded by gene constructs of DNA vaccines that act as target proteins for an immune response. The terms "target protein" and "immunogen" are used interchangeably and refer to a protein against which an immune response can be elicited. The target protein is an immunogenic protein that shares at least an epitope with a protein from the pathogen or undesirable cell-type such as a cancer cell or a cell involved in autoimmune disease against which an immune response is desired. The immune response directed against the target protein will protect the individual against and/or treat the individual for the specific infection or disease with which the target protein is associated.

x. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within +2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

y. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. IL-12

Provided herein is a synthetic, constructs which encode human IL-12 p35 (the α subunit) and p40 (the β subunit). The human IL-12 p35 subunit (SEQ ID NO:2) is a 219 amino acid protein which includes a signal peptide at amino acids 1-22 and a mature protein sequence at positions 23-219. The human IL-12 p40 subunit (SEQ ID NO:4) is a 328 amino acid protein which includes a signal peptide at amino acids 1-22 and a mature protein sequence at positions 23-328. Amino acids 40-90 of the human IL-12 p40 subunit are referred to as the immunoglobulin domain; amino acids 125-217 of the human IL-12 p40 subunit are referred to as the cytokine interleukin-12 p40 C-terminus domain.

In some embodiments, the IL-12 p35 subunit is encoded by a construct comprising a coding sequence on one plasmid and the IL-12 p40 subunit is encoded by a construct comprising a coding sequence on a different plasmid. In some embodiments, the construct which comprises the IL-12 p35 subunit coding sequence and the construct which comprises the IL-12 p40 subunit coding sequence are on the same plasmid but each construct has its own promoter. In some embodiments, the construct which comprises the IL-12 p35 subunit coding sequence and the construct which comprises the IL-12 p40 subunit coding sequence are on the same plasmid and under the control of a single promoter and separated by an TRES sequence. In some embodiments, the construct which comprises the IL-12 p35 subunit coding sequence and the construct which comprises the IL-12 p40 subunit coding sequence are on the same plasmid and under the control of a single promoter and separated by a coding sequence for a proteolytic cleavage site. In some embodiments, the construct which comprises the IL-12 p35 subunit coding sequence and the construct which comprises the IL-12 p40 subunit coding sequence are on the same plasmid and under the control of a single promoter and the subunit are separated by a linker which allows them to be active as a single chain protein HuIL12-opt sequences are optimized sequences that encode human IL-12 subunits. The sequence have lower homology with the host genome to change the RNA structure and avoid criptic regulation sequences. The sequences provide improved mRNA stability and expression.

The HuIL12-opt sequence that is the coding sequence that encodes human IL-12 p35 subunit is disclosed in SEQ ID NO:1. The HuIL12-opt sequence that is the 219 amino acid IL-12 p35 subunit amino acid sequence encoded thereby is disclosed as SEQ ID NO.2. Amino acids 1-22 correspond to the signal peptide. Amino acids 23-219 correspond to the mature protein region.

The HuIL12-opt sequence that is the coding sequence that encodes human IL-12 p40 subunit is disclosed as SEQ ID NO:3. The HuIL12-opt sequence that is the 328 amino acid IL-12 p40 subunit amino acid sequence encoded thereby is disclosed as SEQ ID NO.4. Amino acids 1-22 correspond to the IL-12 signal peptide and amino acids 23-328 make up the mature protein. Analogous sequences for Rhesus IL-12 are RhIL12-opt sequences which are optimized sequences that encode rhesus IL-12 subunits.

In some embodiments, the IL-12 signal peptide of the IL-12 p35 or p40 subunit or both may be replaced with a different signal peptide such as another immunoglobulin signal peptide, for example IgG or IgE (SEQ ID NO:5). Coding sequences that encode the IL-12 signal peptide of the IL-12 p35 or p40 subunit or both may be replaced with coding sequences that encode a different signal peptide such as another immunoglobulin signal peptide, for example IgG or IgE (that is coding sequences that encode SEQ ID NO:5). In some embodiments, the IL-12 p35 signal peptide may be replaced with a different signal peptide such as another immunoglobulin signal peptide, for example IgG or IgE (SEQ ID NO:5). Functional fragments of SEQ ID NO.2 may be free of the IL-12 p35 signal peptide sequence. In some embodiments, coding sequence that encodes the IL-12 p35 signal peptide may be replaced with a coding sequence for different signal peptide such as a coding sequence for another immunoglobulin signal peptide, for example a coding sequence for the signal peptide of IgG or IgE (i.e a coding sequence that encodes SEQ ID NO:5). Nucleic acid sequences that are fragments of SEQ ID NO:1 may be free of the coding sequence for IL-12 p35 signal peptide. Functional fragments of SEQ ID NO.4 may be free of the IL-12 p40 signal peptide sequence. In some embodiments, coding sequence that encodes the IL-12 p40 signal peptide may be replaced with a coding sequence for different signal peptide such as a coding sequence for another immunoglobulin signal peptide, for example a coding sequence for the signal peptide of IgG or IgE (i.e a coding sequence that encodes SEQ ID NO:5). Nucleic acid sequences that are fragments of SEQ ID NO:3 may be free of the coding sequence for IL-12 p40 signal peptide. In calculating homology to SEQ ID NO:1 or SEQ ID NO:3 in coding sequences that do not encode the IL-12 p35 signal peptide or IL-12 p40 signal peptide, respectively, the calculation is base upon a comparison of SEQ ID NO:1 or SEQ ID NO:3 excluding the portion of SEQ ID NO:1 that encode the IL-12 p35 signal peptide or the portion of SEQ ID NO:3 that encodes the IL-12 p40 signal peptide.

3. Plasmid

Provided herein is a vector that is capable of expressing the IL-12 constructs in the cell of a mammal in a quantity effective to modulate an immune response in the mammal. Each vector may comprise heterologous nucleic acid encoding the one or both subunits. The vector may be a plasmid. The plasmid may be useful for transfecting cells with nucleic acid encoding Il-12, which the transformed host cell is cultured and maintained under conditions wherein expression of the IL-12 takes place.

The plasmid may comprise a nucleic acid encoding one or more antigens. The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metalothionein. The promoter may also be a tissue specific promoter, such as a muscle or skin specific promoter, natural or synthetic. Examples of such promoters are described in US patent application publication no. US20040175727, the contents of which are incorporated by reference herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen, San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference in their entireties.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E.coli*). The plasmid may also be pYES2 (Invitrogen, San Diego, Calif.), which may be used for protein production in Saccharomyces cerevisiae strains of yeast. The plasmid may also be of the MAXBAC™ complete baculovirus expression system (Invitrogen, San Diego, Calif.), which may be used for protein production in insect cells. The plasmid may also be pcDNA I or pcDNA3 (Invitrogen, San Diego, Calif.), which may be used for protein production in mammalian cells such as Chinese hamster ovary (CHO) cells.

4. Vaccine

According to some embodiments of the invention, the delivery of a nucleic acid sequence that encodes IL-12 or functional fragments thereof, in combination with a nucleic acid sequence that encodes an immunogen to an individual enhances the immune response against the immunogen. When the nucleic acid molecules that encode the immunogens and IL-12 are taken up by cells of the individual, the immunogen and IL-12 are expressed in cells and the proteins are thereby delivered to the individual. Aspects of the invention provide methods of delivering the coding sequences of the immunogen and IL-12 on a single nucleic acid molecule, methods of delivering the coding sequences of the immunogen and IL-12 on different nucleic acid molecules and methods of delivering the coding sequences of the proteins as part of recombinant vaccines and as part of attenuated vaccines.

According to some aspects of the present invention, compositions and methods are provided which prophylactically and/or therapeutically immunize an individual against a pathogen or abnormal, disease-related cells. The vaccine may be any type of vaccine such as, a live attenuated vaccine, a recombinant vaccine or a nucleic acid or DNA vaccine. By delivering nucleic acid molecules that encode an immunogen and IL-12 or functional fragments thereof the immune response induced by the vaccine may be modulated. The IL-12 constructs are particularly useful when delivered in combination with a nucleic acid molecule that encodes an immunogen such as for example as part of a plasmid or the genome of a recombinant vector or attenuated pathogen or cell. The IL-12 constructs may be used in vaccines prophylactically in order to induce a protective immune response in an uninfected or disease free individual. The IL-12 constructs are particularly useful when delivered to induce a protective immune response in humans. The IL-12 constructs may be used in vaccines therapeutically in order to induce a immune response in an infected or diseased individual. The IL-12 constructs are particularly useful when delivered to induce a therapeutic immune response in humans. In some embodiments, nucleic acid molecules comprising the IL-12 constructs are delivered in a cell free composition. In some embodiments, nucleic acid molecules comprising the IL-12 constructs are delivered in a composition free of cancer cells. In some embodiments, comprising the IL-12 constructs are administered free of any other cytokine.

Provided herein are vaccine capable of generating in a mammal an immune response against pathogens, immunogens expressed on cells associated with disease and other immunogens against which an immune response is desired. The vaccine may comprise each plasmid as discussed above. The vaccine may comprise a plurality of the plasmids, or combinations thereof. The vaccine may be provided to induce a therapeutic or prophylactic immune response.

Genetic constructs may comprise a nucleotide sequence that encodes a target protein or an immunomodulating protein operably linked to regulatory elements needed for gene expression. According to the invention, combinations of gene constructs that include one construct that comprises an expressible form of the nucleotide sequence that encodes a target protein and one construct that includes an expressible form of the nucleotide sequence that encodes an immunomodulating protein are provided. Delivery into a living cell of the DNA or RNA molecule(s) that include the combination of gene constructs results in the expression of the DNA or RNA and production of the target protein and one or more immunomodulating proteins. An enhanced immune response against the target protein results.

The present invention may be used to immunize an individual against pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens that include a stage in the life cycle where they are intracellular pathogens. Table 1 provides a listing of some of the viral families and genera for which vaccines according to the present invention can be made. DNA constructs that comprise DNA sequences that encode the peptides that comprise at least an epitope identical or substantially similar to an epitope displayed on a pathogen antigen such as those antigens listed on the tables are useful in vaccines. Moreover, the present invention is also useful to immunize an individual against other pathogens including prokaryotic and eukaryotic protozoan pathogens as well as multicellular parasites such as those listed on Table 2.

TABLE 1

| Viruses |
| --- |
| Picornavirus Family |
|   Genera: |
|     Rhinoviruses: (Medical) responsible for ~50% cases of the common cold. |
|     Etheroviruses: (Medical) includes polioviruses, coxsackieviruses, echoviruses, and human enteroviruses such as hepatitis A virus. |
|     Apthoviruses: (Veterinary) these are the foot and mouth disease viruses. |
|     Target antigens: VP1, VP2, VP3, VP4, VPG |
| Calcivirus Family |
|   Genera: |
|     Norwalk Group of Viruses: (Medical) these viruses are an important causative agent of epidemic gastroenteritis. |
| Togavirus Family |
|   Genera: |
|     Alphaviruses: (Medical and Veterinary) examples include Sindbis virus, RossRiver virus and Venezuelan Eastern & Western Equine encephalitis viruses. |
|     Reovirus: (Medical) Rubella virus. |
| Flariviridae Family |
|     Examples include: (Medical) dengue, yellow fever, Japanese encephalitis, St. Louis encephalitis and tick borne encephalitis viruses. West Nile virus (Genbank NC001563, AF533540, AF404757, AF404756, AF404755, AF404754, AF404753, AF481864, M12294, AF317203, AF196835, AF260969, AF260968, AF260967, AF206518 and AF202541) |
|     Representative Target antigens: E NS5 C |
| Hepatitis C Virus: (Medical) these viruses are not placed in a family yet but are believed to be either a togavirus or a flavivirus. Most similarity is with togavirus family. |
| Coronavirus Family: (Medical and Veterinary) |
|     Infectious bronchitis virus (poultry) |
|     Porcine transmissible gastroenteric virus (pig) |
|     Porcine hemagglutinating encephalomyelitis virus (pig) |
|     Feline infectious peritonitis virus (cats) |
|     Feline enteric coronavirus (cat) |
|     Canine coronavirus (dog) |
|     SARS associated coronavirus |
|     The human respiratory coronaviruses cause about 40% of cases of common cold. EX. 224E, OC43 Note - coronaviruses may cause non-A, B or C hepatitis |
|     Target antigens: E1 - also called M or matrix protein E2 - also called S or Spike protein |

TABLE 1-continued

Viruses

E3 - also called BE or hemagglutin-elterose glycoprotein (not present in all coronaviruses) N - nucleocapsid
Rhabdovirus Family
    Genera:
    Vesiculovirus, Lyssavirus: (medical and veterinary) rabies
    Target antigen: G protein, N protein
Filoviridae Family: (Medical)
    Hemorrhagic fever viruses such as Marburg and Ebola virus
Paramyxovirus Family:
    Genera:
    Paramyxovirus: (Medical and Veterinary) Mumps virus, New Castle disease virus (important pathogen in chickens)
        Morbillivirus: (Medical and Veterinary) Measles, canine distemper
        Pneumovirus: (Medical and Veterinary) Respiratory syncytial virus
Orthomyxovirus Family (Medical) The Influenza virus
Bunyavirus Family
    Genera:
    Bunyavirus: (Medical) California encephalitis, La Crosse
    Phlebovirus: (Medical) Rift Valley Fever
    Hantavirus: Puremala is a hemahagin fever virus
    Nairvirus (Veterinary) Nairobi sheep disease
    Also many unassigned bungaviruses
Arenavirus Family (Medical) LCM, Lassa fever virus
Reovirus Family
    Genera:
    Reovirus: a possible human pathogen
    Rotavirus: acute gastroenteritis in children
    Orbiviruses: (Medical and Veterinary) Colorado Tick fever,
    Lebombo (humans) equine encephalosis, blue tongue
Retroyirus Family
    Sub-Family:
    Oncorivirinal: (Veterinary) (Medical) feline leukemia virus,
    HTLVI and HTLVII
    Lentivirinal: (Medical and Veterinary) HIV, feline immunodeficiency virus, equine infections, anemia virus
Spumavirinal Papovavirus Family
    Sub-Family:
    Polyomaviruses: (Medical) BKU and JCU viruses
    Sub-Family:
    Papillomavirus: (Medical) many viral types associated with cancers or malignant progression of papilloma.
    Adenovirus (Medical )EX AD7, ARD., O.B. - cause respiratory disease - some adenoviruses such as 275 cause enteritis
Parvovirus Family (Veterinary)
    Feline parvovirus: causes feline enteritis
    Feline panleucopeniavirus
    Canine parvovirus
    Porcine parvovirus
Herpesvirus Family
    Sub-Family:
    alphaherpesviridue
    Genera:
    Simplexvirus (Medical)
    HSVI (Genbank X14112, NC001806),
    HSVII (NC001798)
    Varicella zoster: (Medical Veterinary)
    Pseudorabies
    varicella zoster
    Sub-Family
    betaherpesviridae
    Genera:
    Cytomegalovirus (Medical)
    HCMV
    Muromegalovirus
    Sub-Family.
    Gammaherpesviridae
    Genera:
    Lymphocryptovirus (Medical)
    EBV - (Burkitt's lymphoma)
Poxvirus Family
    Sub-Family:
    Chordopoxviridue (Medical - Veterinary)
    Genera:
    Variola (Smallpox)
    Vaccinia (Cowpox)
    Parapoxivirus - Veterinary
    Auipoxvirus - Veterinary
    Capripoxvirus

TABLE 1-continued

Viruses

Leporipoxvirus
Suipoxviru's
Sub-Family:
Entemopoxviridue
Hepadnavirus Family
   Hepatitis B virus
   Unclassified Hepatitis delta virus

TABLE 2

Bacterial pathogens
   Pathogenic gram-positive cocci include: pneumococcal;staphylococcal; and streptococcal.
   Pathogenic gram-negative cocci include: meningococcal; and gonococcal.
   Pathogenic enteric gram-negative bacilli include: enterobacteriaceae; *pseudomonas*, acinetobacteria and *eikenella*, melioidosis; *salmonella*; shigellosis; hemophilus; chancroid; brucellosis; tularemia; *yersinia (pasteurella)*; *streptobacillus mortiliformis* and *spirillum*; *listeria monocytogenes*; *erysipelothrix rhusiopathiae*; diphtheria, cholera, anthrax; donovanosis (granuloma inguinale); and bartonellosis.
   Pathogenic anaerobic bacteria include: tetanus; botulism; other clostridia; tuberculosis; leprosy; and other mycobacteria.
   Pathogenic spirochetal diseases include: syphilis; -treponematoses: yaws, pinta and endemic syphilis; and leptospirosis.
   Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma, and chromomycosis; and dermatophytosis.
   Rickettsial infections include rickettsial and rickettsioses.
   Examples of mycoplasma and chlamydial infections include: mycoplasma pneumoniae; lymphogranuloma venereum; psittacosis; and perinatal chlamydial infections.
   Pathogenic eukaryotes
   Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

In order to produce a genetic vaccine to protect against pathogen infection, genetic material that encodes immunogenic proteins against which a protective immune response can be mounted must be included in a genetic construct as the coding sequence for the target. Because DNA and RNA are both relatively small and can be produced relatively easily, the present invention provides the additional advantage of allowing for vaccination with multiple pathogen antigens. The genetic construct used in the genetic vaccine can include genetic material that encodes many pathogen antigens. For example, several viral genes may be included in a single construct thereby providing multiple targets.

Tables 1 and 2 include lists of some of the pathogenic agents and organisms for which genetic vaccines can be prepared to protect an individual from infection by them.

In some embodiments, vaccines comprise the optimized IL-12 in combination with one or more DNA vaccine constructs set forth in the following patent documents which are each incorporated herein by reference. In some embodiments, vaccines comprise the optimized IL-12 in combination with (human immunodeficiency virus) an HIV vaccine, an (hepatitis C virus) HCV vaccine, a human papilloma virus (HPV) vaccine, an influenza vaccine or an hTERT-targeted cancer vaccines as disclosed in PCT application PCT/US07/74769 and corresponding U.S. patent application Ser. No. 12/375,518, issued as U.S. Pat. No. 8,168,769. In some embodiments, vaccines comprise the optimized IL-12 in combination with an Influenza vaccines disclosed in PCT application PCT/US08/83281 and corresponding U.S. patent application Ser. No. 12/269,824, issued as U.S. Pat. No. 9,592,285, or PCT application PCT/US11/22642 and corresponding U.S. patent application Ser. No. 12/694,238, issued as U.S. Pat. No. 8,298,820. In some embodiments, vaccines comprise the optimized IL-12 in combination with an HCV vaccines disclosed in PCT application PCT/US08/081627 and corresponding U.S. patent application Ser. No. 13/127,008, issued as U.S. Pat. No. 8,829,174. In some embodiments, vaccines comprise the optimized IL-12 in combination with an HPV vaccines disclosed in PCT application PCT/US10/21869 and corresponding U.S. patent application Ser. No. 12/691,588 issued as U.S. Pat. No. 8,389,706, or U.S. provisional application Ser. No. 61/442,162 which provided priority to issued U.S. Pat. Nos. 9,238,679, 9,403,879. In some embodiments, vaccines comprise the optimized IL-12 in combination with an Smallpox vaccines disclosed in PCT application PCT/US09/045420 and corresponding U.S. patent application Ser. No. 12/473,634, issued as U.S. Pat. No. 8,535,687. In some embodiments, vaccines comprise the optimized IL-12 in combination with an Chikungunya vaccines disclosed in PCT application PCT/US09/039656 and corresponding U.S. patent application Ser. No. 12/936,186, issued as U.S. Pat. No. 8,852,609. In some embodiments, vaccines comprise the optimized IL-12 in combination with an foot and mouth disease virus (FMDV) vaccines disclosed in PCT application PCT/US10/55187 and corresponding U.S. patent application Ser. No. 13/503,828, issued as U.S. Pat. No. 9,109,014, corresponding U.S. patent application Ser. No. 14/816,120, issued as U.S. Pat. No. 10,294,278, and corresponding U.S. patent application Ser. No. 16/416,663. In some embodiments, vaccines comprise the optimized IL-12 in combination with an Malaria vaccines disclosed in U.S. provisional application Ser. No. 61/386,973 which provided priority to published PCT Application No. PCT/US11/53541 and corresponding U.S. patent application Ser. No. 13/876,148. In some embodiments, vaccines comprise the optimized IL-12 in combination with an prostate cancer vaccines disclosed in U.S. provisional application Ser. No. 61/413,176, which provided priority to U.S. Pat. Nos. 8,927,692 and 9,399,056, or U.S. provisional application Ser. No. 61/417,817, which provided priority to U.S. Pat. Nos. 8,927,692; 9,399,056. In some embodiments, vaccines comprise the optimized IL-12 in combination with an human cytomegalovirus (CMV) vaccines disclosed in U.S. provisional application Ser. No. 61/438,089, which provided priority to U.S. Pat. No. 9,243,041. In some embodiments, vaccines comprise the optimized IL-12 in combination with Methicillin-Resistant *Staphylococcus aureus* (MRSA) vaccines disclosed in U.S. Provisional Application Ser. No. 61/569,727, filed on Dec. 12, 2011, entitled "PROTEINS COMPRISING MRSA PBP2A AND FRAGMENTS THEREOF, NUCLEIC ACIDS ENCODING THE SAME, AND COMPOSITIONS AND THEIR USE TO PREVENT AND TREAT MRSA INFECTIONS" and designated its corresponding PCT Application (PCT/US12/69014) and the corresponding U.S. patent application Ser. No. 14/365,071, issued as U.S. Pat. No. 9,750,795, corresponding U.S. patent application Ser. No. 15/675,823, issued as U.S. Pat. No. 10,064,931, and corresponding U.S. patent application Ser. No. 16/111,267, claiming priority to U.S. Provisional Application Ser. No. 61/569,727, each of which are incorporated by reference in their entireties. All patents and patent applications disclosed herein are incorporated by reference in their entireties.

Another aspect of the present invention provides a method of conferring a protective immune response against hyperproliferating cells that are characteristic in hyperproliferative diseases and to a method of treating individuals suffering from hyperproliferative diseases. Examples of hyperproliferative diseases include all forms of cancer and psoriasis.

It has been discovered that introduction of a genetic construct that includes a nucleotide sequence which encodes an immunogenic "hyperproliferating cell"-associated protein into the cells of an individual results in the production of those proteins in the vaccinated cells of an individual. To immunize against hyperproliferative diseases, a genetic construct that includes a nucleotide sequence that encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides; which comprise at least an epitope found on such proteins. In some cases, a hyperproliferative-associated protein is the product of a mutation of a gene that encodes a protein. The mutated gene encodes a protein that is nearly identical to the normal protein except it has a slightly different amino acid sequence which results in a different epitope not found on the normal protein. Such target proteins include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-IA and folate binding proteins or PSA.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and technology as well as epidemiology allow for the determination of probability and risk assessment for the development of cancer in individual. Using genetic screening and/or family health histories, it is possible to predict the probability a particular individual has for developing any one of several types of cancer.

Similarly, those individuals who have already developed cancer and who have been treated to remove the cancer or are otherwise in remission are particularly susceptible to relapse and reoccurrence. As part of a treatment regimen, such individuals can be immunized against the cancer that they have been diagnosed as having had in order to combat a recurrence. Thus, once it is known that an individual has had a type of cancer and is at risk of a relapse, they can be immunized in order to prepare their immune system to combat any future appearance of the cancer.

The present invention provides a method of treating individuals suffering from hyperproliferative diseases. In such methods, the introduction of genetic constructs serves as an immunotherapeutic, directing and promoting the immune system of the individual to combat hyperproliferative cells that produce the target protein. In treating or preventing cancer, embodiments which are free of cells are particularly useful.

The present invention provides a method of treating individuals suffering from autoimmune diseases and disorders by conferring a broad based protective immune response against targets that are associated with autoimmunity including cell receptors and cells which produce "self"-directed antibodies.

T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) that are involved in the disease have been characterized. These TCRs include Vβ-3, Vβ-14, 20 Vβ-17 and Vα-17. Thus, vaccination with a DNA construct that encodes at least one of these proteins will elicit an immune response that will target T cells involved in RA. See: Howell, M. D., et al., 1991 Proc. Nat. Acad. Sci. USA 88:10921-10925; Piliard, X., et al, 1991 Science 253:325-329; Williams, W. V., et al., 1992 J Clin. Invest. 90:326-333; each of which is incorporated herein by reference. In MS, several specific variable regions of TCRs that are involved in the disease have been characterized. These TCRs include Vβ-7, and Vα-10. Thus, vaccination with a DNA construct that encodes at least one of these proteins will elicit an immune response that will target T cells involved in MS. See: Wucherpfennig, K. W., et al., 1990 Science 248:1016-1019; Oksenberg, J. R., et al, 1990 Nature 345:344-346; each of which is incorporated herein by reference.

In scleroderma, several specific variable regions of TCRs that are involved in the disease have been characterized. These TCRs include Vβ-6, Vβ-8, Vβ-14 and Vα-16, Vα-3C, Va-7, Vα-14, Vα-15, Vα-16, Vα-28 and Vα-12. Thus, vaccination with a DNA construct that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al 1987 Sequence of Proteins of Immunological Interest U.S. Department of Health and Human Services, Bethesda Md., which is incorporated herein by reference. In addition, a general method for cloning functional variable regions from antibodies can be found in Chaudhary, V. K., et al, 1990 Proc. Natl. Acad Sci. USA 87:1066, which is incorporated herein by reference.

In addition to using expressible forms of immunomodulating protein coding sequences to improve genetic vaccines, the present invention relates to improved attenuated live vaccines and improved vaccines that use recombinant vectors to deliver foreign genes that encode antigens. Examples of attenuated live vaccines and those using recombinant vectors to deliver foreign antigens are described in U.S. Pat. Nos. 4,722,848; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; and 5,482,713, which are each incorporated herein by reference. Gene constructs are provided which include the nucleotide sequence of the IL-12 constructs or functional fragments thereof, wherein the nucleotide sequence is operably linked to regulatory sequences that can function in the vaccine to effect expression. The gene constructs are incorporated in the attenuated live vaccines and recombinant vaccines to produce improved vaccines according to the invention.

The vaccine may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS), Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example WO9324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more additional adjuvants. An adjuvant may be other genes that are expressed from the same or from an alternative plasmid or are delivered as proteins in combination with the plasmid above in the vaccine. The one or more adjuvants may be proteins and/or nucleic acid molecules that encode proteins selected from the group consisting of: α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, Gly-CAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or a combination thereof. In some embodiments additional adjuvant may be one or more proteins and/or nucleic acid molecules that encode proteins selected from the group consisting of: IL-15, IL-28, CTACK, TECK, MEC or RANTES. Examples of IL-15 constructs and sequences are disclosed in PCT application no. PCT/US04/18962 and corresponding U.S. application Ser. No. 10/560,650, and in PCT application no. PCT/US07/00886 and corresponding U.S. application Ser. No. 12/160,766, and in PCT application no. PCT/US10/048827. Examples of IL-28 constructs and sequences are disclosed in PCT application no. PCT/US09/039648 and corresponding U.S. application Ser. No. 12/936,192. Examples of RANTES and other constructs and sequences are disclosed in PCT application no. PCT/US1999/004332 and corresponding U.S. application Ser. No. 09/622,452. Other examples of RANTES constructs and sequences are disclosed in PCT application no. PCT/US11/024098. Examples of RANTES and other constructs and sequences are disclosed in PCT application no. PCT/US1999/004332 and corresponding U.S. application Ser. No. 09/622,452. Other examples of RANTES constructs and sequences are disclosed in PCT application no. PCT/US11/024098. Examples of chemokines CTACK, TECK and MEC constructs and sequences are disclosed in PCT application no. PCT/US2005/042231 and corresponding U.S. application Ser. No. 11/719,646. Examples of OX40 and other immunomodulators are disclosed in U.S. application Ser. No. 10/560,653. Examples of DR5 and other immunomodulators are disclosed in U.S. application Ser. No. 09/622,452.

The vaccine may further comprise a genetic vaccine facilitator agent as described in U.S. Ser. No. 021,579 filed Apr. 1, 1994, which is fully incorporated by reference.

The vaccine may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polyanions or polyanions to the vaccine formulation.

5. Methods of Delivery the Vaccine

Provided herein is a method for delivering a vaccine including the IL-12 constructs to produce immune responses effective against the vaccine immunogens. The method of delivering the vaccine or vaccination may be provided to induce a therapeutic and prophylactic immune response. The vaccination process may generate in the mammal an immune response against immunogens. The vaccine may be delivered to an individual to modulate the activity of the mammal's immune system and enhance the immune response. The delivery of the vaccine may be the transfection of sequences encoding the immunogen and the IL-12 constructs on one or more nucleic acid molecules. The coding sequences are expressed in cells and delivered to the surface of the cell upon which the immune system recognized and induces a cellular, humoral, or cellular and humoral response. The delivery of the vaccine may be use to induce or elicit and immune response in mammals against the immunogen by administering to the mammals the vaccine as discussed above. The inclusion of the IL-12 constructs results in a more effective immune response.

Upon delivery of the vaccine and plasmid into the cells of the mammal, the transfected cells will express and secrete immunogens and IL-12 encoded by the plasmids injected from the vaccine. These immunogens will be recognized as foreign by the immune system and antibodies will be made against them. These antibodies will be maintained by the immune system and allow for an effective response to subsequent infections. The presence of the IL-12 encoded by the IL-12 constructs results in a greater immune response.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatments

The IL-12 construct may be administered in combination with other proteins or genes encoding one or more of α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-15 (including IL-15 having the signal sequence deleted and optionally including the signal peptide from IgE), MHC, CD80, CD86, IL-1, IL-2, IL-4, IL-5, IL-6, IL-10, IL-18, IL-28, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof or combinations thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

b. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (Inovio Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., issued as U.S. Pat. No. 8,209,006, the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, issued as U.S. Pat. No. 9,452,285, which claims the benefit under 35 USC 119(e) to U.S. Provisional Application Ser. No. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Method of Preparing DNA Plasmids

Provided herein is methods for preparing the DNA plasmids that comprise the DNA constructs and vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, co-pending U.S. provisional application U.S. Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

6. Immunomodulating Compositions and Methods

In some embodiments, the nucleic acid sequences that encode the IL-12 subunits are delivered without the addition of nucleic acid sequences that encode an immunogen. In such methods, the nucleic acid sequences that encode the IL-12 subunits are used as immunotherapeutics which, when expressed to produce functional IL-12, impart a desired immunomodulatory effect on the individual. The nucleic acid sequences that encode the IL-12 subunits are provided and delivered as described above except for the exclusion of nucleic acid sequences that encode an immunogen. In such methods, the nucleic acid sequences that encode the IL-12 subunits may used as immunotherapeutics alone or in combination with other immunomodulatory proteins such as those described above in the section entitled combination treatments.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims Example1

Comparing Expression Levels of phuIL12-opt with phuIL12-nonopt.

Comparison of the expression levels of phuIL12-opt with phuIL12-nonopt was performed to show the important codon/RNA optimization strategies could boost the expression levels/adjuvant effects of a designed synthetic IL-12.

293T cells ($7.5 \times 10^5$) were transfected in 6-well plates with 2 or 4 µg of huIL12-opt or huIL12-nonopt, respectively, using FuGene6 Transfection Reagent (Roche Applied Science, Indianapolis, Ind.) per manufacturer's instructions. DNA and FuGene6 Transfection Reagent were added in sequence to serum-free media at a DNA:FuGene6 ratio of 1 µg DNA:3 µl FuGene6 reagent. The volume of serum-free media was determined by the amount needed to make the entire mixture's total volume equal 200 The mixture was added to each well of cells and incubated for 48 hours at 37° C. in a 5% CO2 environment. At the end of the incubation, the supernatant samples were collected for the ELISA assay.

High protein binding plates (Nunc, Rochester, N.Y.) were coated with 100 µl/well of monoclonal antibody MT86/221 from the human IL-12 ELISA kit (Mabtech, Mariemont, Ohio) and incubated overnight at 4° C. After the incubation, the plates were washed twice with PBST (DPBS with 0.1% Tween 20) and blocked for 1 hour with 200 µl/well of a DPBS solution supplemented with 0.05% Tween 20 and 0.1% BSA. Plates were subsequently washed with PBST. Using manufacturer's instructions, a positive standard was prepared using hIL-12 p70 (Mabtech, Mariemont, Ohio). The positive standard and supernatant samples were added to duplicate wells in volumes of 100 µl/well at dilutions of 1:50, 1:150, 1:450, 1:1350, and 1:4050. The samples and positive standard were diluted using the above blocking solution. The plates were subsequently incubated at 4° C.

overnight. Afterwards, the plates were washed with PBST and incubated with 100 μl/well of mAB MT618-biotin (Mabtech, Mariemont, Ohio) for 1 hour. After incubation, the plates were washed again and incubated for 1 hour with 100 μl/well of Streptavidin-HRP diluted at 1:1000 in blocking buffer. The plates were then washed again with PBST and developed using TMB and 2N H₂SO₄. Plates were read at 450 nm using a photospectrometer.

Figure 1B:
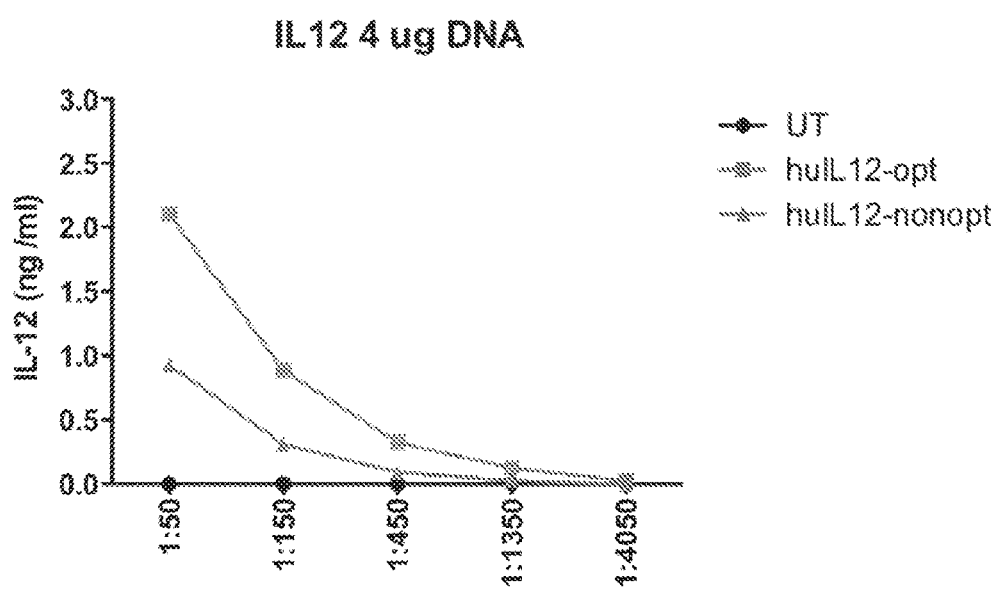

As shown in FIGS. 1A and 1B, the huIL12-opt plasmid exhibits higher levels of expression of IL-12 compared to the huIL12-nonopt. Clearly, the codon/RNA optimization strategies improve the expression of IL-12.

Example2

Enhanced PSA and PSMA-Specific Cellular Immune Responses Elicted by Vaccination with pMacIL12-opt.

Figure 2:
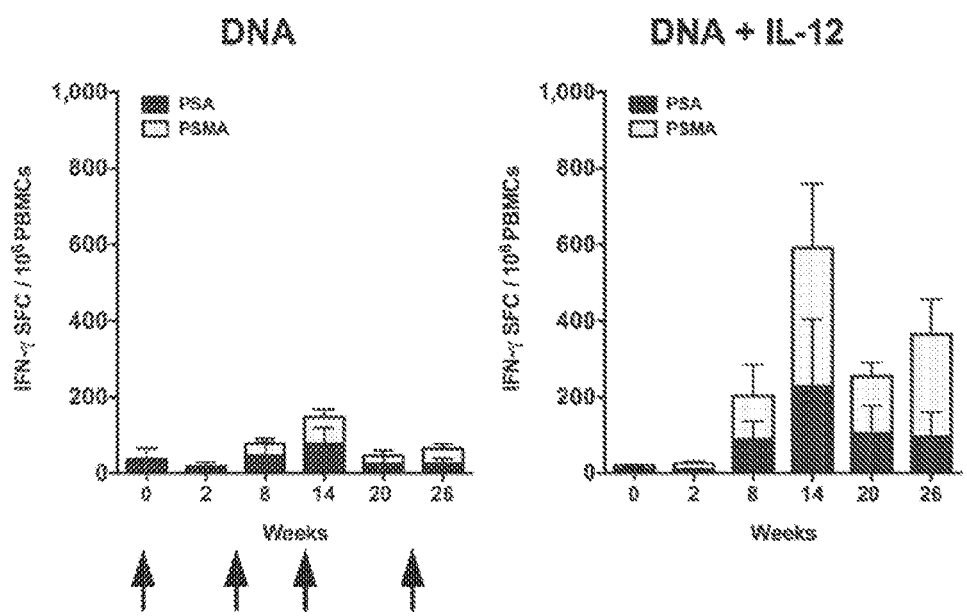
FIG. 2 shows the enhanced PSA and PSMA-specific cellular immune responses in rhesus macaques.

Rhesus macaques were immunized with 1 mg of PSA and PSMA in combination with 0.04 mg of pMacIL-12-opt intramuscularly followed by electroporation with the Cellectra device from Inovio Pharmaceuticals. Two weeks after each immunization rhesus macaques were bled and PBMCs were isolated for the PSA and PSMA-specific IFN-γ ELISpot assay. The group of animals receiving the pMacIL12-opt showed about 3-fold increase in peak response compared to the group of animals not receiving pMacIL12-opt (FIG. 2).

Example3

Enhanced HBV Core and Surface Antigen-Specific Cellular Immune Responses Elicted by Vaccination with pMacIL12-opt.

Rhesus macaques were immunized with 1 mg of core and surface antigens in combination with 0.04 mg of pMacIL-12-opt intramuscularly followed by electroporation with the Cellectra device from Inovio Pharmaceuticals. Two weeks after each immunization rhesus macaques were bled and PBMCs were isolated for the core and surface antigen-specific IFN-γ ELISpot assay. The group of animals receiving the pMacIL12-opt showed increased magnitude and breadth of cellular responses compared to the group of animals not receiving pMacIL12-opt (FIG. 3).

```
SEQUENCE LISTING

SEQ ID NO: 1
ATGTGCCCCGCTCGGTCCCTGCTGCTGGTCGCTACCCTGGTCCTGCTGG

ATCACCTGTCACTGGCTCGAAATCTGCCTGTCGCTACCCCCGATCCTGG

CATGTTCCCCTGCCTGCACCATAGCCAGAACCTGCTGCGGGCCGTGTCC

AATATGCTGCAGAAAGCTAGACAGACACTGGAGTTTTACCCTTGTACTT

CTGAGGAAATCGACCACGAGGATATTACTAAGGACAAAACCTCCACAGT

CGAAGCCTGCCTGCCACTGGAGCTGACCAAGAACGAATCATGTCTGAAT

AGCAGGGAGACTTCCTTCATCACCAACGGGTCTTGCCTGGCTAGTCGCA

AGACCAGCTTCATGATGGCACTGTGCCTGAGCTCCATCTACGAGGATCT

GAAGATGTATCAGGTGGAATTCAAAACCATGAACGCTAAGCTGCTGATG

GACCCTAAACGACAGATCTTTCTGGATCAGAATATGCTGGCAGTGATTG

ACGAGCTGATGCAGGCCCTGAACTTCAATAGCGAAACCGTCCCACAGAA

GTCTAGTCTGGAGGAACCCGACTTTTATAAGACAAAAATCAAGCTGTGC
```

```
                                    -continued

SEQUENCE LISTING

ATTCTGCTGCATGCCTTTCGGATTCGGGCTGTCACTATTGATCGGGTCA

TGTCATACCTGAACGCTTCCTAA

SEQ ID NO: 2
MCPARSLLLVATLVLLDHLSLARNLPVATPDPGMFPCLHHSQNLLRAVS

NMLQKARQTLEFYPCTSEEIDHEDITKDKTSTVEACLPLELTKNESCLN

SRETSFITNGSCLASRKTSFMMALCLSSIYEDLKMYQVEFKTMNAKLLM

DPKRQTFLDQNMLAVIDELMQALNFNSETVPQKSSLEEPDFYKTKIKLC

ILLHAFRIRAVTIDRVMSYLNAS

SEQ ID NO: 3
ATGTGCCATCAGCAGCTGGTCATCTCTTGGTTTAGTCTGGTGTTTCTGG

CTTCTCCACTGGTCGCTATCTGGGAACTGAAAAAGGATGTGTACGTGGT

CGAGCTGGACTGGTATCCAGATGCACCCGGAGAAATGGTGGTCCTGACC

TGCGACACACCCGAGGAAGATGGCATCACTTGGACCCTGGACCAGAGCT

CCGAGGTGCTGGGATCTGGCAAGACACTGACTATTCAGGTCAAAGAATT

CGGGGATGCCGGACAGTACACATGTCACAAGGGCGGGGAGGTGCTGAGT

CACTCACTGCTGCTGCTGCATAAGAAAGAAGACGGCATCTGGTCTACTG

ACATTCTGAAGGATCAGAAAGAGCCTAAGAACAAAACCTTCCTGAGATG

CGAAGCTAAGAATTATAGTGGGAGGTTTACCTGTTGGTGGCTGACCACA

ATCTCAACTGACCTGACCTTTAGCGTGAAATCTAGTAGGGGGTCAAGCG

ATCCACAGGGAGTGACCTGCGGAGCAGCTACACTGAGCGCCGAGCGGGT

GAGAGGAGACAACAAGGAGTACGAATATAGTGTCGAGTGCCAGGAAGAT

TCAGCCTGTCCCGCAGCCGAGGAATCCCTGCCTATCGAAGTGATGGTGG

ACGCTGTGCACAAGCTGAAATACGAAAACTACACATCCTCTTTCTTTAT

TCGCGACATCATTAAGCCAGATCCCCCTAAAAACCTGCAGCTGAAGCCC

CTGAAAAATTCCCGACAGGTGGAGGTCTCTTGGGAATACCCTGATACAT

GGAGCACTCCACATTCTTATTTCAGTCTGACTTTTTGCGTGCAGGTCCA

GGGCAAGAGCAAAAGGGAGAAGAAAGACCGCGTGTTCACCGATAAGACA

TCCGCTACTGTCATCTGTCGAAAAAACGCAAGCATTTCCGTGCGGGCAC

AGGATAGGTATTATTCCAGCAGTTGGTCTGAGTGGGCTTCCGTCCCTTG

TAGTTGA

SEQ ID NO: 4
MCHQQLVISWFSLVFLASPLVAIWELKKDVYVVELDWYPDAPGEMVVLT

CDTPEEDGITWTLDQSSEVLGSGKTLTIQVKEFGDAGQYTCHKGGEVLS

HSLLLLHKKEDGIWSTDILKDQKEPKNKTFLRCEAKNYSGRFTCWWLTT

ISTDLTFSVKSSRGSSDPQGVTCGAATLSAERVRGDNKEYEYSVECQED

SACPAAEESLPIEVMVDAVHKLKYENYTSSFFIRDIIKPDPPKNLQLKP

LKNSRQVEVSWEYPDTWSTPHSYFSLTFCVQVQGKSKREKKDRVFTDKT

SATVICRKNASISVRAQDRYYSSSWSEWASVPCS

SEQ ID NO: 5
MDWTWILFLVAAATRVHS
```

The invention claimed is:

1. A composition for increasing an immune response that comprises a) a nucleic acid sequence that encodes IL-12 p35 subunit and b) a nucleic acid sequence that encodes IL-12 p40 subunit, wherein
the nucleic acid sequence that encodes IL-12 p35 subunit is at least 90% identical to SEQ ID NO:1 and encodes a protein at least 90% identical to SEQ ID NO:2, and
the nucleic acid sequence that encodes IL-12 p40 subunit is at least 90% identical to SEQ ID NO:3 and encodes a protein at least 90% identical to SEQ ID NO:4.

2. The composition of claim 1 comprising
the nucleic acid sequence that encodes IL-12 p35 subunit is at least 97% identical to SEQ ID NO:1 and encodes a protein at least 97% identical to SEQ ID NO:2, and
the nucleic acid sequence that encodes IL-12 p40 subunit is at least 97% identical to SEQ ID NO:3 and encodes a protein at least 97% identical to SEQ ID NO:4.

3. The composition of claim 1 comprising
the nucleic acid sequence that encodes IL-12 p35 subunit is at least 98% identical to SEQ ID NO:1 and encodes a protein at least 98% identical to SEQ ID NO:2, and
the nucleic acid sequence that encodes IL-12 p40 subunit is at least 98% identical to identical SEQ ID NO:3 and encodes a protein at least 98% identical to SEQ ID NO:4.

4. The composition of claim 1 comprising
the nucleic acid sequence that encodes IL-12 p35 subunit is at least 99% identical to SEQ ID NO:1 and encodes a protein at least 99% identical to SEQ ID NO:2, and the nucleic acid sequence that encodes IL-12 p40 subunit is at least 99% identical to SEQ ID NO:3 and encodes a protein at least 99% identical to SEQ ID NO:4.

5. The composition of claim 1 formulated for delivery to an individual using electroporation.

6. The composition of claim 1 wherein the nucleic acid sequence that encodes IL-12 p35 subunit is on a different nucleic acid molecule than the nucleic acid sequence that encodes IL-12 p40 subunit.

7. The composition of claim 1 wherein the nucleic acid sequence that encodes IL-12 p35 subunit is on a plasmid and the nucleic acid sequence that encodes IL-12 p40 subunit is on a different plasmid.

8. The composition of claim 1 wherein the nucleic acid sequence that encodes IL-12 p35 subunit and the nucleic acid sequence that encodes IL-12 p40 subunit are on the same nucleic acid molecule.

9. The composition of claim 1 wherein the nucleic acid sequence that encodes IL-12 p35 subunit and the nucleic acid sequence that encodes IL-12 p40 subunit are on the same plasmid.

10. The composition of claim 1 wherein the nucleic acid sequence that encodes IL-12 p35 subunit and the nucleic acid sequence that encodes IL-12 p40 subunit are on the same nucleic acid molecule and operably linked to different promoters.

11. The composition of claim 1 wherein the nucleic acid sequence that encodes IL-12 p35 subunit and the nucleic acid sequence that encodes IL-12 p40 subunit are on the same plasmid and operably linked to different promoters.

12. The composition of claim 1 further comprising a nucleic acid sequence that encodes an immunogen.

13. The composition of claim 1 further comprising a nucleic acid sequence that encodes an immunogen from a pathogen selected from the group consisting of: HIV, HPV, HCV, Influenza, Smallpox, Chikungunya, foot and mouth disease virus, Malaria, human cytomegalovirus, human respiratory syncytial virus, and MRSA.

14. The composition of claim 1 wherein the nucleic acid sequence that encodes IL-12 p35 subunit and the nucleic acid sequence that encodes IL-12 p40 subunit are incorporated into a viral particle.

15. The composition of claim 1 further comprising a nucleic acid sequence that encodes one or more proteins selected from the group consisting of: IL-15 and IL-28.

16. A method of inducing an immune response against an immunogen comprising administering to an individual, a composition of claim 1 in combination with a nucleic acid sequence that encodes an immunogen in an amount effective to induce an immune response in said individual.

17. The method of claim 16 wherein the composition further comprises a nucleic acid sequence that encodes an immunogen.

18. A composition that comprises a) a nucleic acid sequence that encodes IL-12 p35 subunit or a fragment thereof and b) a nucleic acid sequence that encodes IL-12 p40 subunit or a fragment thereof, wherein the nucleic acid sequence that encodes IL-12 p35 subunit or a fragment thereof is at least 90% identical to SEQ ID NO:1 and encodes a protein at least 90% identical to SEQ ID NO:2, and the nucleic acid sequence that encodes IL-12 p40 subunit or a fragment thereof is at least 90% identical to SEQ ID NO:3 and encodes a protein at least 90% identical to SEQ ID NO:4.

\* \* \* \* \*